United States Patent
Tenhumberg et al.

(10) Patent No.: US 12,012,371 B2
(45) Date of Patent: Jun. 18, 2024

(54) PROCESS OF PREPARING ALCOHOLS

(71) Applicants: thyssenkrupp Industrial Solutions AG, Essen (DE); thyssenkrupp AG, Essen (DE)

(72) Inventors: Nils Tenhumberg, Dortmund (DE); Stefan Gehrmann, Euskirchen (DE); Michael Kleiber, Hattersheim (DE)

(73) Assignees: thyssenkrupp Uhde GmbH, Dortmund (DE); thyssenkrupp AG, Essen (DE)

( * ) Notice: Subject to any disclaimer, the term of this patent is extended or adjusted under 35 U.S.C. 154(b) by 0 days.

(21) Appl. No.: 17/640,092

(22) PCT Filed: Aug. 14, 2020

(86) PCT No.: PCT/EP2020/072827
§ 371 (c)(1),
(2) Date: Mar. 3, 2022

(87) PCT Pub. No.: WO2021/043560
PCT Pub. Date: Mar. 11, 2021

(65) Prior Publication Data
US 2022/0298088 A1   Sep. 22, 2022

(30) Foreign Application Priority Data

Sep. 5, 2019   (DE) ............ 10 2019 213 493.9

(51) Int. Cl.
*C07C 27/08*   (2006.01)
*B01D 3/14*   (2006.01)
(Continued)

(52) U.S. Cl.
CPC ........... *C07C 27/08* (2013.01); *B01D 3/145* (2013.01); *B01D 3/36* (2013.01); *B01D 3/40* (2013.01);
(Continued)

(58) Field of Classification Search
CPC ......... Y02P 20/52; C07C 27/08; C07C 1/043; C07C 7/11; C07C 29/04
See application file for complete search history.

(56) References Cited

U.S. PATENT DOCUMENTS

| | | |
|---|---|---|
| 3,989,762 A | 11/1976 | Ester |
| 4,510,267 A | 4/1985 | Pierantozzi |

(Continued)

FOREIGN PATENT DOCUMENTS

| | | |
|---|---|---|
| CN | 101805242 A | 8/2010 |
| CN | 105251505 A | 1/2016 |

(Continued)

OTHER PUBLICATIONS

English Translation of International Search Report issued in PCT/EP2020/072827, dated Nov. 3, 2020.
U.S. Appl. No. 17/640,069, filed Mar. 3, 2022, Kleiber.

*Primary Examiner* — Sharon Pregler
(74) *Attorney, Agent, or Firm* — thyssenkrupp North America, LLC (57) ABSTRACT

A process can produce alcohols having at least two carbon atoms by catalytic conversion of synthesis gas into a mixture containing alkanes, alkenes, and alcohols. Alkenes are converted into corresponding alcohols in a subsequent step by hydration of the alkanes. Before the hydration and after the catalytic conversion, gas and liquid phases may be separated. Specific catalysts can be employed that have a markedly higher selectivity for alkenes than for alkanes. These catalysts comprise grains of non-graphitic carbon having cobalt nanoparticles dispersed therein. The cobalt nanoparticles have an average diameter $d_p$ from 1 to 20 nm, and an average distance D between nanoparticles is from 2 to 150 nm. The combined total mass fraction of metal $\omega$ in the grains ranges from 30% to 70% by weight of the total mass (Continued)

of the grains of non-graphitic carbon, wherein 4.5 dp/ω > D ≥ 0.25 dp/ω.

18 Claims, 3 Drawing Sheets

(51) Int. Cl.
*B01D 3/36* (2006.01)
*B01D 3/40* (2006.01)
*B01D 53/14* (2006.01)
*B01D 53/22* (2006.01)
*B01D 61/36* (2006.01)
*C07C 1/04* (2006.01)
*C07C 7/00* (2006.01)
*C07C 7/06* (2006.01)
*C07C 7/08* (2006.01)
*C07C 7/11* (2006.01)
*C07C 7/144* (2006.01)
*C07C 29/04* (2006.01)
*C10G 53/08* (2006.01)

(52) U.S. Cl.
CPC ..... *B01D 53/1418* (2013.01); *B01D 53/1425* (2013.01); *B01D 53/1487* (2013.01); *B01D 53/229* (2013.01); *B01D 61/362* (2013.01); *C07C 1/043* (2013.01); *C07C 1/0485* (2013.01); *C07C 7/005* (2013.01); *C07C 7/06* (2013.01); *C07C 7/08* (2013.01); *C07C 7/11* (2013.01); *C07C 7/144* (2013.01); *C07C 29/04* (2013.01); *C10G 53/08* (2013.01); *B01D 2252/205* (2013.01); *B01D 2311/2626* (2013.01); *B01D 2311/2669* (2013.01); *C07C 2521/18* (2013.01); *C07C 2523/72* (2013.01); *C07C 2523/75* (2013.01); *C07C 2523/889* (2013.01); *C10G 2400/20* (2013.01)

(56) References Cited

U.S. PATENT DOCUMENTS

| | | | |
|---|---|---|---|
| 5,237,104 A | 8/1993 | Summerlin | |
| 6,974,842 B1 | 12/2005 | Spena et al. | |
| 6,982,355 B2 | 1/2006 | Abazajian | |
| 8,129,436 B2 | 3/2012 | Tirtowidjojo et al. | |
| 8,354,563 B2 * | 1/2013 | Kharas | C07C 29/151 568/897 |
| 2004/0220443 A1 | 11/2004 | De Graaf et al. | |
| 2007/0004588 A1 * | 1/2007 | Wang | B01J 23/6562 502/343 |
| 2009/0069609 A1 | 3/2009 | Kharas et al. | |
| 2010/0005709 A1 | 1/2010 | Bradin | |
| 2010/0048960 A1 | 2/2010 | Degen et al. | |
| 2010/0069515 A1 | 3/2010 | Tirtowidjojo et al. | |
| 2010/0298125 A1 | 11/2010 | Kim et al. | |
| 2011/0306682 A1 | 12/2011 | Tasaka | |
| 2013/0277478 A1 | 10/2013 | Gronvall | |
| 2014/0135558 A1 | 5/2014 | Kuzma, Jr. et al. | |
| 2014/0142206 A1 | 5/2014 | Karim et al. | |
| 2014/0322095 A1 | 10/2014 | Tasaka | |
| 2016/0348196 A1 | 12/2016 | Achatz et al. | |
| 2018/0254490 A1 * | 9/2018 | Yoo | H01M 4/9083 |
| 2019/0134620 A1 | 5/2019 | Yoo et al. | |

FOREIGN PATENT DOCUMENTS

| | | |
|---|---|---|
| CN | 108014816 A | 5/2018 |
| CN | 108067235 A | 5/2018 |
| DE | 30 40 777 A1 | 5/1982 |
| DE | 40 37 816 A1 | 6/1992 |
| DE | 20 2014 006 837 A1 | 9/2014 |
| DE | 10 2017 208 014 A1 | 11/2018 |
| EP | 0 021 241 B1 | 1/1981 |
| EP | 0 200 880 A1 | 11/1986 |
| EP | 1 419 127 A2 | 5/2004 |
| EP | 1 887 072 A1 | 2/2008 |
| EP | 2 024 304 A2 | 2/2009 |
| EP | 2 070 900 A2 | 6/2009 |
| EP | 2 260 939 A1 | 12/2010 |
| EP | 2 402 418 A1 | 1/2012 |
| EP | 2 653 230 A2 | 10/2013 |
| WO | 2008/048364 A2 | 4/2008 |
| WO | 2014/117783 A1 | 8/2014 |
| WO | 2015/086151 A1 | 6/2015 |
| WO | 2015/086154 A1 | 6/2015 |

\* cited by examiner

Product distribution after HA synthesis and subsequent hydration (150°C, 60bar)

Fig. 4

Product distribution after HA synthesis and subsequent hydration (50°C, 60bar)

PROCESS OF PREPARING ALCOHOLS

CROSS REFERENCE TO RELATED APPLICATIONS

This application is a U.S. National Stage Entry of International Patent Application Serial Number PCT/EP2020/072827, filed Aug. 14, 2020, which claims priority to German Patent Application No. DE 10 2019 213 493.9, filed Sep. 5, 2019, the entire contents of both of which are incorporated herein by reference.

FIELD

The present disclosure generally relates to processes for producing alcohols having at least two carbon atoms by catalytic conversion of synthesis gas into a mixture containing alkenes, alcohols, and alkanes, wherein alkenes present in this mixture are converted into alcohols in at least one subsequent step.

BACKGROUND

EP 0 021 241 B1 discloses a process for producing mixtures of acetic acid, acetaldehyde, ethanol and alkenes having two to four carbon atoms by reacting synthesis gas containing carbon monoxide and hydrogen in the gas phase over supported catalysts, wherein the catalysts contain rhodium and 0.1% to 5.0% by weight of sodium or potassium. The oxygen-containing compounds and the alkenes are formed in a molar ratio of 1:1 to 2.5:1. The selectivity of the employed catalysts for the alcohols is relatively poor. Reaction at a pressure of 20 bar, a temperature of 275° C. and a ratio of carbon monoxide to hydrogen in the synthesis gas of 1:1 forms more than 20% of acetic acid, about 12-20% of acetaldehyde, about 5% to 10% of ethene, and a relatively high proportion of propene of in some cases more than 20%, varying proportions of methane and just a few percent of ethanol, for instance 2.5% to 7%. This known process seeks to produce mixtures of oxygen-containing C2 compounds and a high proportion of low molecular weight alkanes and to reduce the methane proportion. Processes for separating the compound classes from the resulting mixture are not described.

U.S. Pat. No. 6,982,355 B2 describes an integrated Fischer-Tropsch synthesis for producing linear and branched alcohols and alkenes, wherein initially a light fraction and a heavy fraction are separated from one another, the light fraction is contacted with a dehydration catalyst to obtain a light fraction containing alkenes and alkanes which is then further divided into fractions containing C5-C9 and C10-C13 alkenes and alkanes and these are subsequently reacted with synthesis gas partly to afford the aldehydes having the corresponding chain lengths. The aldehydes present in the alkane fraction are subsequently reacted with hydrogen to produce the corresponding alcohols which remain in the alkane fraction. In a first distillation these alcohols are separated from the alkanes and in a further distillation the individual alcohols are obtained from the C5-C9 fraction and the C10-C13 fraction. The alkanes of the corresponding fractions can be dehydrogenated to afford the alkenes. Catalysts used in Fischer-Tropsch synthesis include cobalt, iron, ruthenium or other group VIIIB transition metals, optionally on an oxidic support such as silicon dioxide, aluminum oxide or titanium oxide.

CN108067235A describes catalysts for the production of alkenes from synthesis gas which contain cobalt and cobalt carbide as the active component, lithium as an additive and one or more further metals selected from manganese, zinc, chromium and gallium. The reaction forms not only the alkenes but also higher alcohols. When using these catalysts the selectivity for an alkene mixture is said to be up to 40% and for a mixture of alcohols 30%. Straight-chain alkenes having 2 to 30 carbon atoms and primary alcohols having corresponding chain lengths are obtained. The product mixture contains predominantly alkanes and alkenes and, depending on the catalyst, about 20% to 25% of alcohols, wherein methanol, alcohols having 2 to 5 carbon atoms and higher alcohols having 6 or more carbon atoms are formed, wherein the latter group of alcohols form the predominant proportion and are usually formed to an extent of more than 50%. The publication does not elaborate on the separation of the various products present in the mixture.

CN108014816A describes catalysts for the reaction of carbon monoxide with hydrogen to produce mixed primary alcohols and alkenes. It employs catalysts based on cobalt, in particular dicobalt carbide and manganese, on an activated carbon support which may contain additions of cerium, copper, zinc or lanthanum. Primary alcohols and alkenes having 2 to 30 carbon atoms are formed. The catalysts used here are said to have a high selectivity for alkenes, and it is mentioned that the alkenes formed may be further converted to alcohols by hydroformylation. Depending on the type of catalyst used the catalytic conversion of the synthesis gas forms about 23% to 28% by weight of alkanes, about 36% to 41% by weight of alkenes and about 20% to 21% by weight of higher alcohols, wherein about 8% by weight of methane and about 2% to 5% by weight of carbon dioxide and about 1% to 2% by weight of methanol are additionally formed.

U.S. Pat. No. 8,129,436 B2 describes a process for producing an alcohol mixture from synthesis gas, wherein a mixture of alcohols and oxygen-containing compounds are obtained. It is proposed to strip the product mixture with a methanol-containing stream to remove a proportion of the carbon dioxide as well as inert gases present in the product stream. It is also possible to carry out a downstream dehydration to convert a portion of the ethanol and optionally propanol formed into the corresponding alkenes. The conversion of the synthesis gas uses potassium-modified molybdenum sulfide catalysts. This known process affords very complex product mixtures which do not contain alkenes but do contain relatively small amounts of alkanes and not only C2-C5 alcohols but in some cases also higher proportions of methanol and many other oxygen-containing compounds such as aldehydes, carboxylic acids, ketones, esters, ethers and also mercaptans and alkyl sulfides.

US 2010/0005709 A1 describes alternative fuel compositions containing ethanol, isopropanol and butanols, wherein synthesis gas is initially converted into a C2-C4-alkene stream by a Fischer-Tropsch synthesis and these alkenes are subsequently hydrated. The alcohols obtained may be blended with gasoline to obtain fuel compositions. The reaction of synthesis gas described in this document affords only about 39% of hydrocarbons having 2 to 4 carbon atoms while about 40% of higher hydrocarbons, cycloalkanes and aromatic compounds of C5 to C20, such as are typically present in gasoline or diesel, are formed. The hydration of the C2-C4 alkenes can only afford a maximum of 39% of alcohols, wherein these are exclusively secondary alcohols and tertiary butanol. Methanol, 1-propanol and 1-butanol are not formed. This known process employs iron-manganese catalysts containing proportions of zinc oxide and potassium oxide in a variant of the Fischer- Tropsch synthesis. This reaction forms almost exclusively C2-C4-alkenes and 9.6% of methane and 15.7% of C2-C4-alkanes while forming no alcohols in the primary process, with the result that the alcohols are only obtained in a further step through hydration of the alkenes. Since the product mixture is subsequently mixed with gasoline to form a fuel, it is not absolutely necessary to separate the alkanes or the compounds having 5 carbon atoms or longer carbon chains.

Thus a need exists to develop an improved process for producing alcohols having at least two carbon atoms by catalytic conversion of synthesis gas, wherein the complex product mixture of alcohols, alkenes and alkanes may be converted into downstream products in a targeted manner, thus making it possible to produce a high-quality product/high-quality products for the fuel market and/or the chemical industry. A need also exists for a process of the aforementioned type where the purification of the complex product mixture is made easier.

DETAILED DESCRIPTION

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents. Moreover, those having ordinary skill in the art will understand that reciting "a" element or "an" element in the appended claims does not restrict those claims to articles, apparatuses, systems, methods, or the like having only one of that element, even where other elements in the same claim or different claims are preceded by "at least one" or similar language. Similarly, it should be understood that the steps of any method claims need not necessarily be performed in the order in which they are recited, unless so required by the context of the claims. In addition, all references to one skilled in the art shall be understood to refer to one having ordinary skill in the art.

According to the invention the conversion of the alkanes into alcohols is carried out in at least one subsequent step by hydration of the alkenes.

This consecutive conversion of the alkenes results in a targeted multi-stage synthesis of alcohols from synthesis gas having a substantially higher yield.

Compared to the catalytic processes for producing higher alcohols from synthesis gas that are hitherto known from the prior art the two-stage synthesis according to the invention has the advantage of higher alcohol yields.

The synthesis of higher alcohols generally provides a mixture of primary alcohols. Including hydration in the process makes it possible to selectively form secondary alcohols and thus widen the product spectrum.

A more uniform product is obtained from the complex product mixture, thus leading to advantages in the purification process and in marketing logistics.

The consecutive conversion of the initially likewise obtained alkenes into alcohols additionally has the advantage that the separation of alkanes and alkenes, which is challenging due to similar physical properties, may potentially be avoided and the alkanes may be separated from the product mixture more easily.

Hydration of alkenes to afford the corresponding alcohols is a known reaction for preparing alcohols and is used industrially for example for producing isopropanol from propene. With the exception of ethene the hydration of the linear alkenes results predominantly in the formation of secondary alcohols. Isobutene is hydrated to afford tertiary butanol, a tertiary alcohol.

There are essentially two known industrial processes for hydration of alkanes to afford the corresponding alcohols, on the one hand direct hydration and alternatively indirect hydration.

In direct hydration the alkene is reacted with water over an acidic catalyst to afford the respective alcohol. Hydration of alkenes to alcohols is an equilibrium reaction. High pressures and low temperatures shift the equilibrium of the exothermic reaction to the product side in favor of the alcohols. Indirect hydration of alkenes is carried out in a two-stage reaction. The alkene is initially reacted with sulfuric acid to afford mono- and dialkyl sulfates and subsequently hydrolyzed to afford the alcohol.

Industrially, ethanol is produced predominantly by fermentation of carbohydrates, for example sugars, from corn, sugar beet, grain or wheat. Synthetic ethanol may be produced from ethene by direct hydration. The direct hydration of ethene is carried out in the gas phase over "solid" phosphoric acid (SPA catalysts), for example at 250-300° C. and 50-80 bar. The hydration of ethene is an equilibrium reaction, and high pressure and low temperature favor the exothermic formation of ethanol. Indirect hydration of ethene is no longer performed industrially.

Various known processes are available for the direct hydration of propene. Low-temperature, high-pressure processes (130-180° C., 80-100 bar) with sulfonated polystyrene ion exchange catalysts for example, high-temperature, high-pressure processes (270-300° C., 200 bar) with reduced tungsten oxide catalysts for example and processes in the gas phase (250° C., 250 bar, $WO_3$—$SiO_2$ catalyst, ICI process/170-260° C., 25-65 bar, phosphoric acid catalyst on $SiO_2$, Hüls process). Direct hydration of propene with steam under high pressure is performed in Canada, Mexico and Western Europe. The indirect hydration of propene may employ not only propene but also the C3 stream from refinery offgas having a propene concentration of 40-60%.

2-Butanol (secondary butyl alcohol) may be produced from butene or MTBE raffinate by direct hydration or indirect hydration. 2-Butanol is used to produce methyl ethyl ketone (MEK).

WO 2015/086151 A1 describes by way of example a process by which synthesis gas may be provided by purifying and conditioning various gas streams formed in a metallurgical works. The process described in the present invention for the catalytic synthesis of alcohols having at least two carbon atoms, also referred to in the present application as "higher alcohols", is suitable, for example, for conversion of synthesis gas from such sources. However, all other suitable synthesis gas sources may in principle be considered for the process according to the invention.

In the context of the present invention an overall process allowing production of higher alcohols (having two or more carbon atoms) in good yield starting from synthesis gas was developed. The present application describes processes which, starting from the product mixture obtained during the reaction of synthesis gas comprising carbon monoxide and/or carbon dioxide and hydrogen, offer economic, technological and/or ecological advantages over known processes, in particular over mere separation with subsequent individual marketing of the products/groups of substances. Particular attention was paid to optimization of product separation in accordance with the synthesis steps. This relates inter alia to the respective physical process conditions (pressure, temperature) and the establishment of preferred/technically tolerable reactant ratios for the synthesis steps while taking into account economic boundary conditions in particular.

Due to the large plant capacities which are necessary for example for the utilization of significant quantities of metallurgical gas but also for other synthesis gas sources it is preferable to employ processes affording products having sufficiently large (potential) markets. It is therefore of particular interest here to consider commodity chemicals employable for example in the plastics or fuels sectors.

A possible preferred variant of the process according to the invention comprises initially subjecting the first mixture of alkanes, alkenes and alcohols obtained after catalytic conversion of synthesis gas and preferably after separation of the unconverted synthesis gas to separation of the alkanes and alkenes from the alcohols and only subsequently hydrating the alkenes in this second mixture.

The alcohols are separable from the alkenes and alkanes at little cost and complexity. By contrast, the alkenes are separable from the alkanes only at considerable cost and complexity. The consecutive hydration of the alkenes to alcohols thus facilitates the separation process of alkenes and alkanes.

A preferred development of the process according to the invention comprises initially separating the second mixture of alkanes and alkenes into two or more fractions having different numbers of carbon atoms and only subsequently hydrating the respective individual fractions separately from another to obtain the corresponding alcohols from the alkenes in the respective fractions.

The separation of the alkene/alkane mixture into the individual Cx cuts/alkenes can be advantageous since this allows separate hydration of the individual alkenes. Alkenes whose respective hydration products are particularly suitable for the fuel market, or alkenes that may be hydrated under mild reaction conditions or inexpensively, may be selectively converted to the respective alcohols. Alkenes for which there is an appropriate alkene market can be separated from the respective C cut and marketed. Furthermore, the reaction conditions for the hydration of the individual Cx cuts or alkenes can be chosen independently of one another. For example, a hydration of the C2 fraction/of ethene could be dispensed with and the ethene could instead be used for other applications in the chemical industry. This moreover makes it possible to obtain a relatively pure alkane stream which may be used for synthesis gas production or power generation. However, this mode of operation requires a separate plant for hydration of the alkenes for each C cut or batchwise hydration of the different fractions.

In an alternative preferred variant of the process according to the invention the second mixture comprising the alkanes and alkenes contains a mixture of C2-C4 alkanes or a mixture of C2-C5 alkenes which is subsequently hydrated to the corresponding alcohols as a mixture. This variant thus comprises hydration of an alkane/alkene mixture without first providing for separation of this mixture into different fractions having different numbers of carbon atoms.

Having regard to the reaction conditions for the hydration of such an alkene/alkene mixture it must be noted that the conventional industrial processes are optimized for the conversion of the individual alkenes and differ from one another in terms of the choice of catalyst and the reaction conditions. For this step of hydration of the alkene/alkane mixture this variant of the invention therefore preferably employs process conditions which allow conversion of all alkenes or promote conversion of the favored alkenes to the respective alcohols. Compared to the aforementioned process variant hydration of the alkene mixture has the advantage that only one plant is required for the hydration/batchwise hydration of the various fractions can be avoided.

After the hydration the alkanes are separated from the alcohols formed. The alkanes stream remaining after separation of the alcohols may subsequently be used for producing synthesis gas or power generation for example.

In a preferred development of the process according to the invention the conditions for the hydration of the alkane/alkene mixture in terms of the choice of catalyst and the reaction conditions, especially temperature and pressure, at which the hydration reaction is carried out are selected such that the hydration of propene and/or 1-butene is favored over that of ethene. It was found that the catalysts employed in the context of the present invention in the production of higher alcohols by catalytic conversion of synthesis gas result in the formation of predominantly propene as the alkene. The CO selectivity of the conversion of synthesis gas into alkenes decreases in the order 1-propene>1-butene>ethene. The industrial processes for hydration of 1-propene and 1-butene proceed under milder reaction conditions than those of ethene so that in this process it might potentially be advantageous to concentrate on the hydration of propene and to neglect the hydration of ethene/potentially dispense with the hydration of ethene.

In a preferred development of the process according to the invention direct hydration is performed at elevated temperatures and at elevated pressure. Wide temperature ranges and wide pressure ranges are in principle possible here depending on the other conditions selected. The hydration is generally carried out in the presence of an acid catalyst.

For example the hydration of the alkanes may be performed at temperatures above 80° C., in particular above 100° C., for example at temperatures in the range from 100° C. to 180° C., preferably at 120° C. to 150° C., and/or at a pressure of 5 bar to 150 bar, in particular at a pressure of 10 bar to 100 bar, preferably at a pressure of 50 bar to 100 bar, for example at a pressure of 70 bar to 80 bar. The hydration of propene and of 1-butene proceeds under similar respective reaction conditions, for example at the aforementioned temperatures and pressures. Industrial direct hydration of the propene achieves conversions of for example up to 75% per pass. For the direct hydration of the alkene/alkane mixture the invention therefore proposes using the reaction conditions for the hydration of propene and 1-butene as a reference. It is also conceivable in principle to perform the hydration of the alkene/alkane mixture in a plurality of consecutive reactors with different catalysts and/or different reaction conditions and intermediate separation of the alcohols formed.

A third possible preferred variant of the process according to the invention provides for carrying out the hydration of the alkenes with the mixture of alkanes, alkenes and alcohols without separating the alcohols from this mixture beforehand. The hydration of the alkanes in the mixture of alcohols, alkenes and alkanes obtained from the conversion of the synthesis gas without preceding separation of the alcohols present in this mixture may for example offer the advantage that the reaction mixture is already at a relatively high pressure of for example about 60 bar and therefore merely requires preheating to the reaction temperature.

At a reaction temperature of about 150° C. for example the hydration of the alkenes to the alcohols is thermodynamically preferred. Experiments in the context of the synthesis of the higher alcohols with specific catalysts and subsequent hydration and also calculations for an equilibrium reactor show clearly that a conversion of the alkenes and the primary $C_{3+}$ alcohols to the secondary alcohols takes place when performing the hydration at elevated temperature (for example up to 150° C.) and elevated pressure of for example 2 bar to 100 bar. Especially propene and 1-butanol are converted predominantly to isopropanol and 2-butanol. Ethene is hydrated to ethanol.

A preferred development of the process according to the invention provides that after the hydration the alkanes are separated from the product mixture obtained and the remaining mixture of alcohols is optionally purified and/or separated into individual fractions of alcohols or individual alcohols. This in turn has the advantage that in principle only alcohols and alkanes remain after the hydration, even in the variant described above where the alcohols already obtained in the conversion of the synthesis gas in the first step are not separated before the second step of hydration. This in turn means that the mixture contains only two substance classes which are easy to separate from one another while the separation of alkanes and alkanes would be substantially more difficult.

A preferred development of the process according to the invention provides that before the hydration of the alkenes to the corresponding alcohols and after the catalytic conversion of the synthesis gas it comprises at least one step which separates the product mixture obtained in this reaction into a gas phase and a liquid phase, wherein the liquid phase is used for the subsequent hydration of the alkenes to the alcohols. The gas phase separated at this point may contain for example unconverted CO and $H_2$ as well a $CO_2$, $CH_4$ and $N_2$. In a preferred variant of the process according to the invention the gas phase obtained in this separation process which generally contains the recited unconverted gases may be at least partially recycled to the step of catalytic conversion of the synthesis gas in order thus to increase the yield of the overall process through renewed conversion of the recycled reactant gases to higher alcohols.

It is alternatively also possible in principle to perform the hydration of the alkenes before a separation of the product mixture obtained after the conversion of the synthesis gas into a gas phase and a liquid phase. In this case the hydration is preferably carried out directly in a reactor arranged downstream of the synthesis of higher alcohols and without preceding separation of the product mixture. Propene and butene may be hydrated at for example about 150° C. while higher temperatures of for example about 230° C. to 260° C. are advantageous for the hydration of ethene. The hydration may be carried out at a lower temperature than the preceding conversion of the synthesis gas, wherein temperatures of for example 120° C. to 150° C. may be selected for the hydration. It may therefore be advantageous to cool the product mixture to temperatures in this order of magnitude for the hydration.

Experiments, calculations and simulation of the synthesis of higher alcohols with subsequent hydration show that under the reaction conditions of the synthesis of higher alcohols the dehydration of the alcohols to the alkenes is thermodynamically preferred. When the reaction conditions of the synthesis of higher alcohols are for example about 280° C. and about 60 bar, virtually complete conversion of the alcohols into the corresponding alkenes is possible.

By contrast, at a reaction temperature in the order of for example about 50° C. the hydration of the alkenes to the alcohols is thermodynamically preferred. Experiments in the context of the synthesis of the higher alcohols with specific catalysts and calculations/simulations of the subsequent hydration for an equilibrium reactor show clearly that a conversion of the alkenes and the primary alcohols to the secondary alcohols takes place when performing the hydration at for example about 50° C. and a pressure of about 60 bar. Especially propene and 1-butanol are converted predominantly to isopropanol and 2-butanol. Ethene is hydrated to ethanol.

However, it must be noted in this purely thermodynamic view that the industrial processes for hydration are generally carried out at reaction temperatures of 130-260° C. It is therefore to be expected that at 50° C. the reaction proceeds at a markedly reduced reaction rate. This process variant is therefore less suitable for the hydration of the alkenes (or performable only under certain boundary conditions).

On the contrary, preference is thus to be given to one of the abovementioned variants where the synthesis of higher alcohols is followed initially by separation into a gas phase and a liquid phase, wherein the product mixture is cooled after the synthesis of higher alcohols from the synthesis gas.

The process according to the invention especially comprises the following three preferred process variants:

In variant 1 the process preferably comprises the steps of:
production of higher alcohols (having at least two carbon atoms) and of alkenes by catalytic conversion of synthesis gas;
separation of the obtained product mixture into a gas phase and a liquid phase;
separation of the alkenes and optionally of the alkanes formed as byproducts from the alcohols obtained;
optionally purification of the alcohol mixture separated from the alkenes and alkanes into individual compounds or groups of compounds, in particular ethanol, propanols, butanols and optionally methanol;
separation of the mixture of alkenes and alkanes into two or more fractions, each having a different number of carbon atoms, in particular C2, C3 and C4 fraction;
separate hydration of the respective fractions obtained previously, preferably by reaction with water, to obtain respective mixtures of alcohols and alkanes having the same number of carbon atoms;

optionally purification of the respective mixtures of alcohols and alkanes having the same number of carbon atoms into individual alcohols and alkanes.

In variant 2 the process preferably comprises the steps of:

production of higher alcohols (having at least two carbon atoms) and of alkenes by catalytic conversion of synthesis gas;

separation of the obtained product mixture into a gas phase and a liquid phase;

separation of the alkenes and optionally of the alkanes formed as byproducts from the alcohols obtained;

optionally purification of the alcohol mixture separated from the alkenes and alkanes into individual compounds or groups of compounds, in particular ethanol, propanols, butanols and optionally methanol;

hydration of the mixture of the alkenes and alkanes previously separated from the alcohols, preferably by reaction of the alkenes with water to obtain a mixture of alcohols and alkanes;

separation of the alkanes from the mixture after the hydration and optionally combination of the alcohols thus obtained with the alcohols previously obtained in the synthesis;

optionally purification of the alcohol mixture obtained into individual compounds or groups of compounds, in particular ethanol, propanols, butanols and optionally methanol.

In variant 3 the process preferably comprises the steps of:

production of higher alcohols (having at least two carbon atoms) and of alkenes by catalytic conversion of synthesis gas;

separation of the obtained product mixture into a gas phase and a liquid phase;

hydration of the previously obtained product mixture of the liquid phase comprising alcohols, alkenes and alkanes, preferably by reaction with water, wherein the alkenes in the mixture are hydrated to afford the corresponding alcohols;

separation of the alkenes from the alcohols obtained;

optionally purification of the alcohol mixture separated from the alkanes into individual compounds or groups of compounds, in particular ethanol, propanols, butanols and optionally methanol.

A fourth process variant where the hydration of the alkenes is already carried out after the conversion of the synthesis gas and before the separation of the obtained product mixture into a gas phase and a liquid phase is alternatively possible.

In variant 4 the process preferably comprises the steps of:

production of higher alcohols (having at least two carbon atoms) and of alkenes by catalytic conversion of synthesis gas;

hydration of the obtained product mixture comprising alcohols, alkenes and alkanes, wherein the alkenes in the mixture are hydrated to the corresponding alcohols;

separation of the obtained product mixture into a gas phase and a liquid phase;

separation of the alkanes and optionally of the alkenes present from the alcohols obtained;

optionally purification of the alcohol mixture separated from the alkanes into individual compounds or groups of compounds, in particular ethanol, propanols, butanols and optionally methanol.

In all four of the aforementioned process variants an at least partial recycling of the gas phase to the synthesis of the higher alcohols after the gas-liquid separation is advantageous.

The hydration of the alkenes may be performed not only by the aforementioned process variants but also by a combination of two or more of the aforementioned process variants. For example the composition of the product mixture of higher alcohols (having at least two carbon atoms) and alkenes initially obtained by catalytic conversion of synthesis gas can be shifted by process variant 4 and, after separation of the thus obtained product mixture into a gas phase and a liquid phase, the alkenes present in the liquid phase may be hydrated to the corresponding alcohols using for example one of the process variants 1, 2 or 3. The combination of the two process variants can for example favor the isomerization of the primary alcohols to secondary alcohols. The isomerization of the primary alcohols to the secondary alcohols proceeds via the dehydration of the primary alcohols to the corresponding alkenes as intermediate products. The dehydration preferably proceeds at higher temperatures than the hydration.

The provision of the synthesis gas for the catalytic conversion into alcohols according to the invention may comprise not only the preparation of the synthesis gas but also the purification and the conditioning of the synthesis gas. Suitable feeds include not only fossil fuels, such as natural gas, coal, but also CO-rich and $CO_2$-rich gases, for example from steel or cement works, and hydrogen. It is also possible to obtain the synthesis gas used from biomass. The hydrogen is preferably produced in a sustainable manner by means of renewable energy and/or low $CO_2$ emissions, for example by water electrolysis or methane pyrolysis. The electricity for operating the hydrogen production is preferably generated using renewable energy.

According to the invention the catalytic synthesis of the higher alcohols from synthesis gas may be performed for example at reaction temperatures of 200° C. to 360° C., preferably at temperatures of 220° C. to 340° C., more preferably at 240° C. to 320° C., in particular at 260° C. to 300° C., for example at about 280° C. In addition, this reaction may be performed for example at a reaction pressure of 10 bar to 110 bar, in particular at 30 bar to 90 bar, preferably at 50 bar to 70 bar, for example at about 60 bar. The obtained product mixture of unconverted synthesis gas, alcohols, alkenes and alkanes may be cooled to relatively low temperatures of for example 150° C. or less, in particular to below 130° C., preferably to below 110° C. or to even lower temperatures of less than 80° C., for example about 40° C. to 20° C., especially to about 30° C., and separated into a gas phase and a liquid phase. The gas phase contains predominantly the unconverted synthesis gas and any inert components present (for example nitrogen) and the methane formed as a byproduct. The gas phase is usually recycled to the synthesis of the higher alcohols. A purification or conditioning of the gas phase, for example conversion of the methane formed as a byproduct into synthesis gas, may optionally be additionally provided for.

The liquid phase contains predominantly the alcohols, alkenes and alkanes formed Reducing the pressure to less than 50 bar, in particular to less than 30 bar, preferably to less than 20 bar, more preferably to less than 10 bar, for example 3 to 1 bar, preferably to about 1 bar, allows the alkenes and alkanes to be evaporated and separated from the mixture. However, other methods known to those skilled in the art for separating the alkenes and alkanes from the alcohols are also suitable here. It may be advantageous for economic and/or ecological optimization of the process to convert the alkanes into synthesis gas, for example via a partial oxidation, steam reforming or autothermal reforming, and to recycle said gas into the process. The alkanes may optionally also be dehydrated to afford the corresponding alkenes and subsequently likewise hydrated to increase the yield of alcohols. The alcohols remain in the liquid phase and after separation of the co-produced water are optionally marketed as a product mixture, for example as a fuel additive, or separated into the individual alcohols in a distillation.

There is also the option of hydrating the alkenes after separation of the alkanes from the respective Cx cuts. This gives the advantage of a relatively pure starting material concentration as well the option of performing the dehydration under industrially familiar conditions for the respective alkene. However, due to the apparatus complexity and energy cost of the separation of alkanes and alkenes this option may only be performed under certain boundary conditions.

The various options for integration of the consecutive conversion of the alkenes to alcohols into the process concept for synthesis of the higher alcohols each differ in terms of the composition of the reaction mixture and the prevailing process conditions, such as temperature and pressure, and in terms of the manner and juncture of the separation of the alcohols, alkenes and alkanes from the synthesis gas. Integrating the hydration of the alkenes into the process concept for the synthesis of the higher alcohols provides the opportunity to utilize the existing temperature and pressure levels of the catalytic synthesis of higher alcohols for the hydration.

The catalytic synthesis of the higher alcohols from synthesis gas preferentially forms primary alcohols. Formation of secondary alcohols is hardly observed. By contrast, the hydration of the linear alkenes preferentially forms secondary alcohols such as isopropanol and 2-butanol (with the exception of ethanol). The synthesis of higher alcohols and the consecutive hydration of the alkenes thus differ in terms of their product spectrum.

If isomerization of the primary alcohols to secondary alcohols is desired it is in contrast necessary to select a suitable process concept which ensures isomerization of primary alcohols to secondary alcohols.

The possible isomerization of the primary alcohols to secondary alcohols allows for a separation of the alcohols from the hydrocarbon mixture (alkenes, alkanes), i.e. the abovementioned process variants 1 and 2 are preferentially suitable for the hydration. The alcohols can be separated from the alkenes and alkanes at little cost and complexity. By contrast, the alkenes are separable from the alkanes only at considerable cost and complexity. The consecutive hydration of the alkenes to alcohols thus facilitates the separation process of alkenes and alkanes.

A preferred development of the process according to the invention provides that the catalytic conversion of the synthesis gas is followed by processing of the product mixture comprising at least the steps of:
  absorption of the alkenes, alkanes and, at least in part, the alcohols in a high-boiling hydrocarbon or hydrocarbon mixture as an absorption medium;
  separation of the gases not absorbed into the absorption medium as a gas phase;
  separation of an aqueous phase from the organic phase of the absorption medium, preferably by decanting;
  optional distillative removal of the alcohols from the aqueous phase;
  desorption of the alkenes, alkanes and alcohols from the absorption medium.

A preferred development of the process according to the invention provides that the separation of the alcohols from the alkenes and alkanes or the separation of the alcohols from the alkanes before or after the hydration of the alkanes may comprise at least the steps of:
  separation of the alcohols in at least one distillation column at an elevated pressure of preferably at least 10 bar;
  removal of the water from the alcohol fraction, preferably using a molecular sieve, by extractive distillation, by pervaporation or by azeotropic distillation.

In the context of a development of the present invention specific cobalt-containing catalysts combining properties of a methanol synthesis catalyst and a Fischer-Tropsch catalyst were developed. In this way the catalytic conversion of synthesis gas forms a product mixture which contains not only the higher alcohols (especially ethanol, propanol and butanol) but also high concentrations of hydrocarbons (especially C2-C4 alkenes and C1-C4 alkanes), water and $CO_2$.

Employed here is a catalyst which comprises grains of non-graphitic carbon having cobalt nanoparticles dispersed therein, wherein the cobalt nanoparticles have an average diameter $d_p$ in the range from 1 nm to 20 nm and the average distance D between individual cobalt nanoparticles in the grains of non-graphitic carbon is in the range from 2 nm to 150 nm and $\omega$, the combined total mass fraction of metal in the grains of non-graphitic carbon is in the range from 30% by weight to 70% by weight of the total mass of the grains of non-graphitic carbon, wherein $d_p$, D and $\omega$ satisfy the following relationship: $4.5\ dp/\omega \geq D\ 0.25\ dp/\omega$.

The process according to the invention particularly preferably employs a catalyst doped with a metal selected from Mn, Cu or a mixture thereof, wherein the grains of non-graphitic carbon have a molar ratio of cobalt to doped metal in the range from 2 to 15.

In experiments in the context of the present invention it has been found that the aforementioned grains of non-graphitic carbon having cobalt nanoparticles dispersed therein are obtainable from aqueous solutions of metallic precursors and organic carbon sources by combined spray drying or freeze drying of the aqueous solution and thermal treatment of the resulting intermediate at moderate temperatures.

Non-graphitic carbon may be identified by those skilled in the art via TEM analysis (PW Albers, Neutron scattering study of the terminating protons in the basic structural units of non-graphitizing and graphitizing carbons, Carbon 109 (2016), 239-245, page 241, FIG. 1c).

Compared to present knowledge and also to the descriptions known from the literature the aforementioned catalysts surprisingly have a significantly higher selectivity for alkenes than for alkanes (for example of the order of about 3:1). The product mixture thus comprises not only the alcohols with the alkenes but also further products of value, the material rather than energetic utilization of which is advantageous from an economic and ecological standpoint.

In connection with an advantageous development of the invention a further important aspect is also the separation of the products of value from the relatively complex product mixture at the reactor outlet. In addition to the products of value alcohols and alkenes the product mixture may also contain residual gases (depending on the input gas: $H_2$, CO, $CO_2$, $N_2$) and byproducts (especially alkanes, $CO_2$ and $H_2O$).

Figure 1:
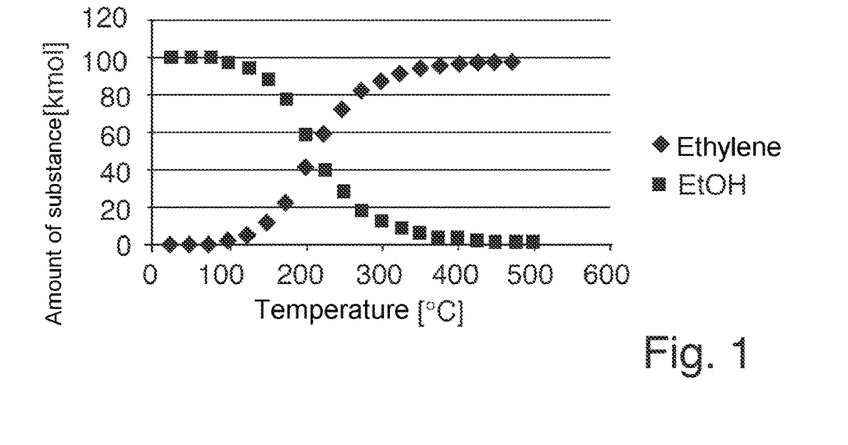
FIG. 1 is a graph of temperature dependence of the equilibrium of the hydration of ethene to ethanol at a pressure of 60 bar.
Figure 2:
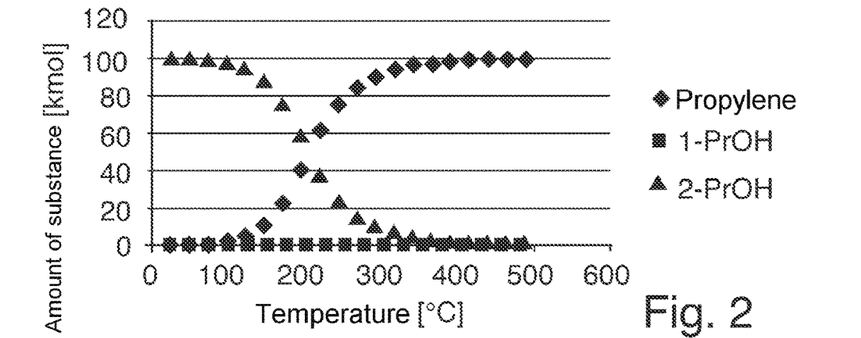
FIG. 2 is graph of temperature dependence of the equilibrium of the hydration of propene to propanol at a pressure of 60 bar.
Figure 3:
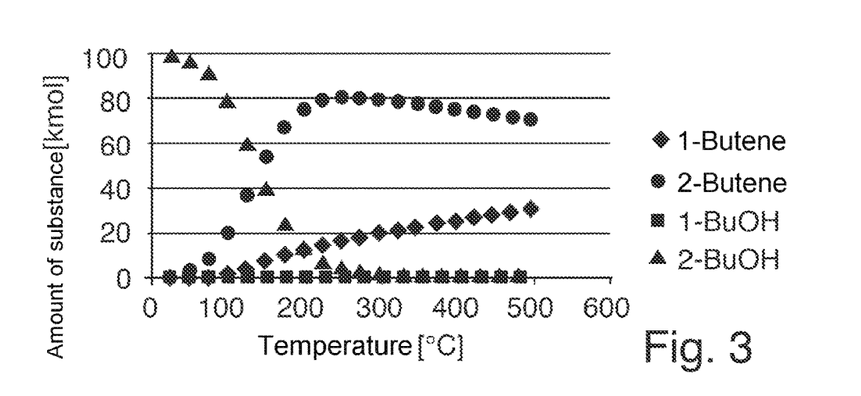
FIG. 3 is a graph of temperature dependence of the equilibrium of the hydration of butene to butanol at a pressure of 60 bar.

In the following, reference is first made to FIG. 1 to 3 and the temperature dependence of the thermodynamic equilibrium is more particularly elucidated with reference to these representations. FIG. 1 shows graphically the temperature dependence of the equilibrium of ethene and ethanol at a pressure of 60 bar, FIG. 2 the temperature dependence of the equilibrium of propene propanol at a pressure of 60 bar and FIG. 3 the temperature dependence of the equilibrium of butene and butanol at a pressure of 60 bar. FIG. 1 to 3 show that at the reaction conditions of 150° C. and 60 bar the thermodynamic equilibrium is on the side of the alcohols for all three reactions. The unconverted alkenes may together with the alkanes be converted for example into synthesis gas and recycled into the process. Indirect hydration of the alkanes may be preferable on account of the alkene/alkane mixture.

FIG. 2 further shows that it is 2-propanol that is practically exclusively formed, while the amount of 1-propanol is negligibly small.

It is apparent from FIG. 3 that at thermodynamic equilibrium at temperatures up to about 150° C. predominantly 2-butanol is formed, while at higher temperatures predominantly 2-butene is formed. The amount of 1-butene formed at higher temperatures is substantially lower compared to 2-butene, but continuously increases somewhat at still higher temperatures of 200° C. to 500° C. 1-Butanol is formed only in negligibly small amounts independently of temperatures.

Figure 4:
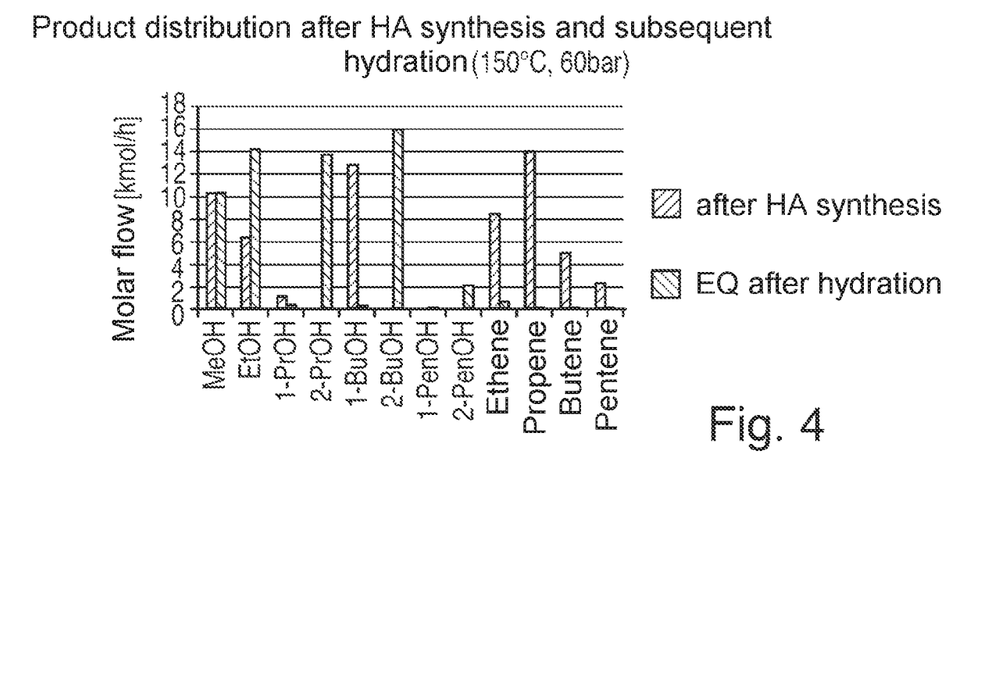
FIG. 4 is a graph of an exemplary product distribution after catalytic conversion of synthesis gas to higher alcohols and subsequent hydration of the product mixture consisting of the alcohols, alkenes, and alkanes at a temperature of 150° C. and a pressure of 60 bar.

In the following, reference is made to FIG. 4. In the embodiment of FIG. 4 the hydration of the reaction mixture consisting of alcohols, alkenes and alkanes was performed at a temperature of 150° C. As can be demonstrated using simulations and calculations of thermodynamic equilibrium the mixture of alkanes and primary alcohols is under these reaction conditions virtually completely converted into secondary alcohols. It is thought that the isomerization of the primary alcohols to the secondary alcohols proceeds via formation of the alkenes as intermediates. The hydration of the product mixture of the synthesis of higher alcohols from alcohols and alkenes thus makes it possible to shift the product spectrum in the direction of the secondary alcohols. The industrial hydration of propene and 1-butene proceeds at reaction temperatures of 120 to 150° C.

In the following, reference is made to FIG. 5. These two diagrams are used to elucidate for example the respective product distribution after the catalytic synthesis of higher alcohols according to the invention and the immediately subsequent step of hydration of the alkenes, wherein the hydration was performed at different temperatures in the two exemplary embodiments.

Figure 5:
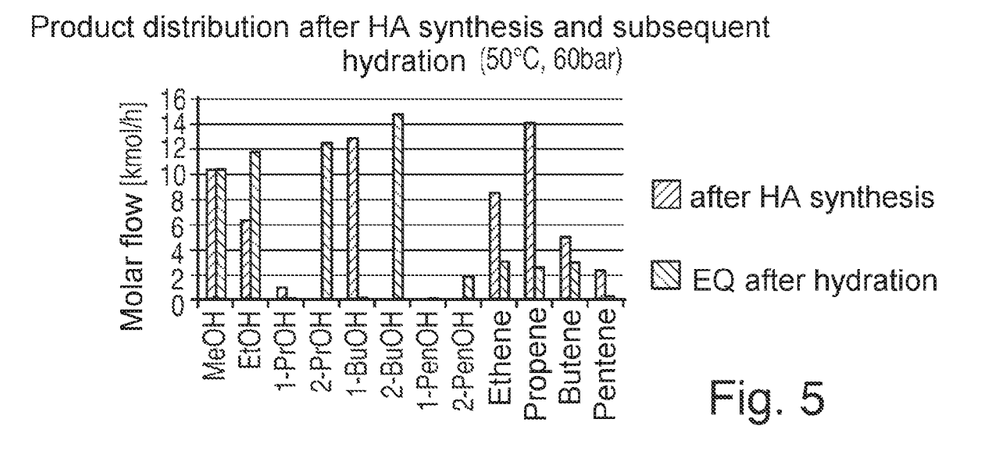
FIG. 5 is a graph of an exemplary product distribution after catalytic conversion of synthesis gas to higher alcohols and subsequent hydration of the product mixture consisting of the alcohols, alkenes, alkanes, and synthesis gas at a temperature of 50° C. and a pressure of 60 bar.

In the exemplary embodiment of FIG. 5 the hydration was simulated at a temperature of 50° C. This temperature is thermodynamically preferred as can be demonstrated using simulations and calculations. However, it must be noted in this purely thermodynamic view that the industrial processes for hydration are generally carried out at reaction temperatures of 130-260° C. It is therefore to be expected that at 50° C. the reaction proceeds at a markedly reduced reaction rate.

The product distribution in FIG. 5 shows that after the first reaction step, the synthesis of the higher alcohols, the alcohols formed are predominantly ethanol and 1-butanol and the alkanes formed are predominantly 1-propene and 1-butene as well as some ethene and 1-pentene. After the hydration at 50° C. the main products present are ethanol, 2-propanol and 2-butanol, while alkenes only remain in relatively small amounts, primarily butene and some pentene.

The hydration of the product mixture of the synthesis of higher alcohols from alcohols and alkenes thus makes it possible in principle to shift the product spectrum in the direction of the secondary alcohols. The industrial hydration of propene and 1-butene proceeds at reaction temperatures of 120 to 150° C.

Figure 6:
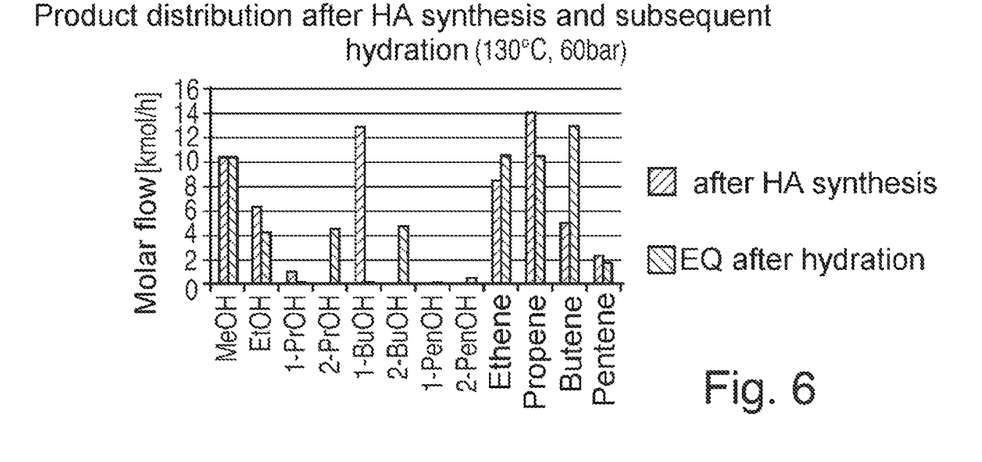
FIG. 6 is a graph of an exemplary product distribution after catalytic conversion of synthesis gas to higher alcohols and subsequent hydration of the product mixture consisting of the alcohols, alkenes, alkanes, and synthesis gas at a temperature of 130° C. and a pressure of 60 bar.

FIG. 6 therefore shows in a similar diagram to FIG. 5 the respective product distribution after the synthesis of higher alcohols and also after the subsequent hydration, but in the present case at a higher temperature of 130° C. during the hydration. The product distribution of the alcohols and alkenes after the first synthesis step is the same as in FIG. 5.

The simulation of the thermodynamic equilibrium at 130° C. shows that propene and pentene are partially converted into the corresponding secondary alcohols. By contrast, ethanol and 1-butanol are dehydrated to afford the respective alkenes. 1-Propanol and 1-butanol are also partially isomerized to 2-propanol and 2-butanol. The isomerization of the linear alcohols to the secondary alcohols proceeds via formation of the alkenes as intermediates.

This simulation thus shows that according to the reaction conditions, product composition and reaction conditions this variant may be advantageous for the hydration of individual alkenes, thus making it possible to increase the yield of these alcohols. By contrast, for other alcohols this variant may have the result that the alcohol yield is reduced and the alcohols are preferentially converted into alkenes. This process variant may ultimately also achieve a shift in the product spectrum. Supplemental to the description of process variant 4 the product mixture thus obtained may be converted into alcohols in a further hydration reaction, for example by combination of process variant 4 with one of the process variants 1, 2 or 3.

In the following, reference is made to FIG. 7. The reaction conditions of the hydration of ethene and of propene are similar to the synthesis of the higher alcohols so that in an alternative variant of the invention it may optionally be advantageous to perform the hydration of the alkenes directly in a reactor arranged downstream of the catalytic synthesis of higher alcohols and without preceding separation of the product mixture. Here it is advantageous that the reaction mixture is already at a similar temperature and pressure level in the alcohol synthesis as is required for the conversion in the hydration. The reaction mixture need not be cooled and compressed to a low temperature and low pressure (for example 30° C., 1 bar) but rather may be converted directly.

Figure 7:
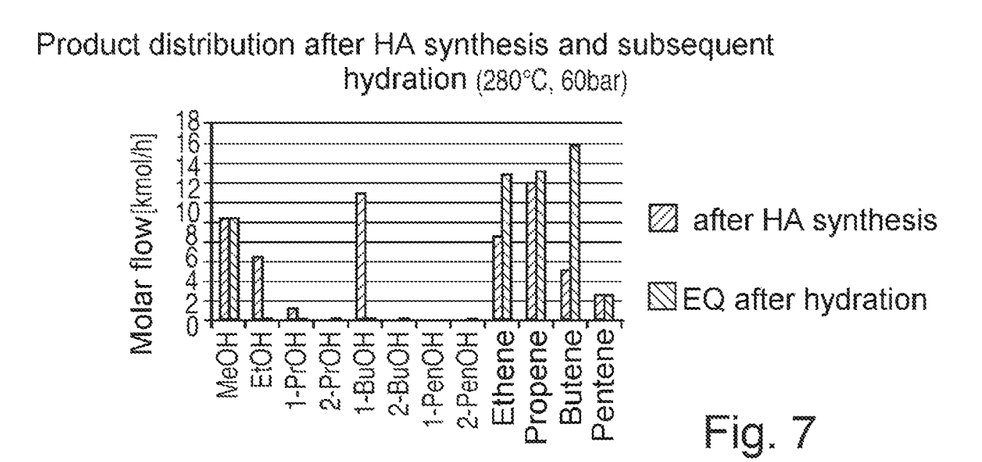
FIG. 7 is a graph of an exemplary product distribution after catalytic conversion of synthesis gas to higher alcohols and subsequent dehydration of the product mixture consisting of the alcohols, alkenes, alkanes, and synthesis gas at a temperature of 280° C. and a pressure of 60 bar.

However, simulations show that under the reaction conditions of the catalytic synthesis of higher alcohols the dehydration of the alcohols to the alkenes is thermodynamically preferred (see FIG. 7). The synthesis of the higher alcohols was simulated using the current experimental conversions and selectivities from catalyst development and testing. The subsequent dehydration/hydration was calculated with an equilibrium reactor. The results clearly show that under the reaction conditions of the catalytic synthesis of higher alcohols (280° C., 60 bar) an almost complete conversion of the alcohols into the corresponding alkenes is possible.

According to observation of the thermodynamic alcohol/alkene equilibrium the direct hydration of the product mixture of the catalytic synthesis of higher alcohols does not lead to an increase in alcohol yield. The formation of alkanes instead of the desired alcohols is preferred in some cases.

Conclusion: The consecutive hydration of the alkenes formed as byproducts in the catalytic synthesis of higher alcohols makes it possible to increase the alcohol yield with suitable reaction management. This equilibrium reaction further makes it possible in principle to convert the complex reaction mixture of primary alcohols and alkenes into secondary alcohols (with the exception of ethanol) by means of dehydration and hydration steps. The reduction of the products results in a small number of purification steps of the individual products and facilitates the marketing of the products of the higher alcohols synthesis.

Example 1

Example 1 which follows specifies an exemplary product composition obtained in the catalytic conversion of synthesis gas by the process according to the invention using a catalyst which comprises grains of non-graphitic carbon having cobalt nanoparticles dispersed therein, wherein the cobalt nanoparticles have an average diameter $d_p$ in the range from 1 nm to 20 nm and the average distance D between individual cobalt nanoparticles in the grains of non-graphitic carbon is in the range from 2 nm to 150 nm and $\omega$, the combined total mass fraction of metal in the grains of non-graphitic carbon is in the range from 30% by weight to 70% by weight of the total mass of the grains of non-graphitic carbon, wherein $d_p$, D and $\omega$ satisfy the following relationship: $4.5\ dp/\omega > D \geq 0.25\ dp/\omega$. The catalyst used showed a high C2-C4 selectivity and alcohols, alkenes, and alkanes were formed. The CO selectivity in respect of the conversion to alcohols is about 28%, the CO selectivity in respect of the conversion to alkenes is about 32%. The precise CO selectivities of the catalytic conversion of synthesis gas are apparent from table 1 which follows. The selectivities reported in table 1 were normalized to the products detected in the catalytic tests (C1-C5 alcohols, C1-C5 alkenes and C1-C5 alkanes, CO2). The analysis of the CO conversion indicates that, in addition to the recited products detected, long-chain C6+ alcohols, C6+ alkenes and C6+ alkanes, and in some cases aldehydes, are also formed.

TABLE 1

| | Selectivity [CO selectivity] |
|---|---|
| $CO_2$ | 9.8 |
| Methane | 17.9 |
| Ethane | 4.6 |
| Propane | 4.3 |
| Butane | 3.0 |
| Pentane | 0.3 |
| Ethene | 6.0 |
| 1-Propene | 15.1 |
| 1-Butene | 7.2 |
| Pentene | 4.2 |
| Methanol | 3.7 |
| Ethanol | 4.6 |
| 1-Propanol | 1.1 |
| 2-Propanol | 0.00 |
| 1-Butanol | 18.3 |
| Alkanes (C2-C5) | 12.2 |
| Alkenes (C2-C5) | 32.5 |
| Higher alcohols | 24.0 |

This example employed a pulverulent catalyst. The catalyst may alternatively also be pressed into tablets for example.

Table 1 above shows that the catalytic conversion of synthesis gas according to the invention affords a relatively high proportion of alcohols in addition to the alkenes. The proportion of alkanes in the product mixture is lower in comparison. In the hydration step which follows the alkenes may likewise be converted to alcohols so that inclusive of the subsequent hydration step the synthesis gas may be converted into alcohols with an overall CO selectivity of virtually 60%, wherein primary alcohols (methanol, ethanol, 1-propanol and 1-butanol) are obtained from the alcohol synthesis and ethanol and secondary alcohols (2-propanol, 2-butanol and optionally 2-pentanol) are obtained from the hydration step and wherein the methanol content is relatively low. Such an alcohol mixture is suitable for example as a fuel additive for blending with gasoline. Separation into the individual alcohols is alternatively possible.

Example 2

A possible process for separating the product mixture obtained in the catalytic conversion of synthesis gas is described below by way of example. The exemplary separation process described below describes the separation of the mixture of alcohols, alkenes and alkanes obtained by the reaction of the synthesis gas from the gas phase and its subsequent separation into a mixture of alcohols and a mixture of hydrocarbons. When using the different process variants and converting the product mixture obtained, the individual steps of this process for separating the product mixture can be varied and adapted to the product mixture obtained after the conversion.

Inert Gas Removal

Catalytic conversion of a synthesis gas stream under the conditions of the process according to the invention affords a product stream at a temperature of 280° C. and a pressure of 60 bar. This is initially decompressed to a pressure of 5 to 20 bar, preferably to about 10 bar, in a turbine to generate electrical energy which may be used for the power requirements of the process.

The subsequent gas-liquid separation, which serves in particular to separate the inert gases (nitrogen) and unreacted components of the synthesis gas (hydrogen, carbon monoxide, carbon dioxide and methane), is carried out by absorption of the product stream in a diesel oil (reference component dodecane) or alternatively in an alkane or a hydrocarbon mixture having a relatively low viscosity of less than 10 mPas at room temperature for example and preferably having a relatively high boiling point of more than 200° C. in particular. The water is not absorbed but rather is largely condensed as the second liquid phase.

The two liquid phases (organic phase and aqueous phase) can then be separated in a decanter, the hydrocarbons barely, but the alcohols partially, passing into the aqueous phase. The alcohols may be distilled out of the water again as azeotropes by means of a first column for example. Alcohols and hydrocarbons are then desorbed from the diesel oil, which may be done in a column. The diesel oil may be recycled into the absorption process after desorption. At relatively low inert gas factions in the product stream of the catalytic conversion of synthesis gas a condensation of the low-boiling components may alternatively also be contemplated.

Separation of Alcohols/Hydrocarbons

The subsequent separation of alcohols and hydrocarbons is carried out by distillation in a second column, preferably at a high pressure of 10 bar to 40 bar for example, in order that the C3 fractions remain condensable even in the presence of any residues of inert gas. This separation is preferably carried out such that the hydrocarbons are practically completely removed from the alcohol fraction at the column bottom, while smaller alcohol contents (in particular methanol) in the hydrocarbons may be tolerated. This process may optionally also be assisted by a solubility-based membrane.

Preparation of the Hydrocarbons

In a third distillation column the hydrocarbons are obtained overhead at elevated pressure of for example 5 bar to 20 bar while the remaining water and the alcohols dissolved therein are obtained in the bottoms and separated. This stream can be recycled to the first distillation column to recover the alcohols. The condenser of the column may be a partial condenser for example. The outputs of the column are a gas phase of hydrocarbons and inerts, a liquid phase of hydrocarbons and an aqueous phase which may be returned to the column as reflux.

Dewatering of the Alcohol Fraction

The alcohol fraction may have a water content of about 10% for example. This water may be removed using a molecular sieve for example.

A contemplated alternative method for removing the water from the alcohol fraction is extractive distillation for example with ethylene glycol, though this requires a further separation step since the water is pulled into the bottoms by the ethylene glycol while the alcohols methanol and ethanol are obtained overhead practically free from water. About half of the propanol and all of the butanol remain in the bottoms and these C3-C4 alcohols must likewise be removed from the ethylene glycol overhead in a subsequent column.

A third suitable alternative is pervaporation. Water passes selectively through a membrane and is withdrawn in vaporous form as permeate. Energy consumption is even lower than for a molecular sieve.

A further alternative method would be an azeotropic distillation, for example with butane or pentane as a selective additive.

What is claimed is:

1. A two-stage process for producing alcohols having at least two carbon atoms by catalytic conversion of synthesis gas into a first mixture containing alkenes in a first stage, alcohols, and alkanes, wherein the alkenes present in the first mixture are subsequently converted into alcohols by hydration of the alkenes in a second stage.

2. The process of claim 1 comprising:
separating the alkanes and the alkenes in the first mixture from the alcohols to form a second mixture; and
only subsequently hydrating the alkanes in the second mixture.

3. The process of claim 2 comprising initially separating the second mixture of the alkanes and the alkenes into two or more fractions having different numbers of carbon atoms and only subsequently hydrating at least one of the individual fractions to obtain a corresponding alcohol from the alkene in the fraction.

4. The process of claim 3 comprising separating the second mixture of the alkanes and the alkenes at least into a C2 fraction, a C3 fraction, and a C4 fraction.

5. The process of claim 2 wherein the second mixture contains a mixture of C2-C4 alkenes or C2-C5 alkenes that is hydrated to corresponding alcohols as a mixture.

6. The process of claim 1 comprising hydrating the alkenes with the first mixture of alkanes, alkenes, and alcohols without separating the alcohols from the first mixture beforehand.

7. The process of claim 2 comprising selecting conditions for hydration of the second mixture in terms of choice of catalyst and reaction conditions including temperature and pressure at which a hydration reaction is performed such that hydration of propene and/or 1-butene is favored over hydration of ethene.

8. The process of claim 1 wherein hydration occurs at temperatures above 80° C. and/or at a pressure of 5 bar to 150 bar.

9. The process of claim 8 comprising separating the alkanes from a product mixture that is obtained from the hydration.

10. The process of claim 1 wherein before hydration of the alkenes to corresponding alcohols and after the catalytic conversion of the synthesis gas, the process comprises separating a product mixture obtained into a gas phase and a liquid phase, wherein the liquid phase is used for subsequent hydration of alkenes to alcohols.

11. The process of claim 10 wherein the gas phase is at least partially recycled to the catalytic conversion of the synthesis gas.

12. The process of claim 1 wherein after the catalytic conversion of the synthesis gas and after subsequent hydration of alkenes to alcohols, the process comprises separating a product mixture that is obtained into a gas phase and a liquid phase, wherein the liquid phase contains at least the alcohols.

13. The process of claim 1 comprising at least partially converting at least one of alkenes or primary alcohols into secondary alcohols in the hydration.

14. The process of claim 12 wherein the gas phase obtained in the separation is at least partially recycled to the catalytic conversion of the synthesis gas.

15. The process of claim 1 wherein after the catalytic conversion of the synthesis gas, the process comprises processing a product mixture as follows:
at least partially absorbing the alkenes and alcohols in a high-boiling hydrocarbon or a hydrocarbon mixture as an absorption medium;
separating gases not absorbed into the absorption medium as a gas phase;
separating an aqueous phase from an organic phase of the absorption medium; and
desorbing the alkenes, the alkanes, and the alcohols from the absorption medium.

16. The process of claim 1 wherein before or after hydration of the alkenes, the separation of the alcohols from the alkanes comprises:
separating the alcohols in at least one distillation column at an elevated pressure of at least 10 bar; and
removing water from an alcohol fraction by extractive distillation, by pervaporation, or by azeotropic distillation.

17. The process of claim 1 wherein the catalytic conversion of the synthesis gas employs a catalyst that comprises grains of non-graphitic carbon having cobalt nanoparticles dispersed therein, wherein the cobalt nanoparticles have an average diameter $d_p$ in a range from 1 nm to 20 nm, wherein an average distance D between individual cobalt nanoparticles in the grains of non-graphitic carbon is in a range from 2 nm to 150 nm, wherein a combined total mass fraction w of metal in the grains of non-graphitic carbon is in a range from 30% by weight to 70% by weight of a total mass of the grains of non-graphitic carbon, wherein $4.5\ d_p/\omega > D \geq 0.25\ d_p/\omega$.

18. The process of claim 17 wherein a material of the catalyst is doped with a metal selected from Mn, Cu, or a mixture thereof, wherein the grains of non-graphitic carbon have a molar ratio of cobalt to doped metal in a range from 2 to 15.

\* \* \* \* \*